United States Patent
Hewett

(10) Patent No.: US 11,205,414 B2
(45) Date of Patent: Dec. 21, 2021

(54) NONINVASIVE NEURAL STIMULATION THROUGH AUDIO

(71) Applicant: BrainFM, Inc., Chicago, IL (US)

(72) Inventor: Adam Hewett, Chicago, IL (US)

(73) Assignee: BRAINFM, INC., Chicago, IL (US)

( * ) Notice: Subject to any disclaimer, the term of this patent is extended or adjusted under 35 U.S.C. 154(b) by 356 days.

(21) Appl. No.: 16/276,961

(22) Filed: Feb. 15, 2019

(65) Prior Publication Data
US 2020/0265827 A1 Aug. 20, 2020

(51) Int. Cl.
*G10K 11/18* (2006.01)
*A61N 7/00* (2006.01)

(52) U.S. Cl.
CPC ...... *G10K 11/18* (2013.01); *A61N 2007/0026* (2013.01); *A61N 2007/0073* (2013.01)

(58) Field of Classification Search
CPC .................. G10K 11/18; G10K 15/02; A61N 2007/0073; A61N 2007/0026; A61N 7/00
See application file for complete search history.

(56) References Cited

U.S. PATENT DOCUMENTS

| | | | |
|---|---|---|---|
| 3,712,292 A | 1/1973 | Zentmeyer, Jr. | |
| 4,141,344 A | 2/1979 | Barbara | |
| 4,191,175 A | 3/1980 | Nagle | |
| 4,227,516 A | 10/1980 | Meland et al. | |
| 4,315,502 A | 2/1982 | Gorges | |
| 4,777,529 A | 10/1988 | Schultz et al. | |
| 5,135,468 A | 8/1992 | Meissner | |
| 5,213,562 A | 5/1993 | Monroe | |
| 5,289,438 A | 2/1994 | Gall | |
| 5,586,967 A | 12/1996 | Davis | |
| 7,674,224 B2 | 3/2010 | Hewett | |
| 2001/0049480 A1 | 12/2001 | John et al. | |
| 2007/0084473 A1 | 4/2007 | Hewett | |
| 2010/0005685 A1 | 1/2010 | Russell | |
| 2010/0056854 A1 | 3/2010 | Chang | |
| 2012/0251989 A1 | 10/2012 | Wemore | |
| 2013/0046546 A1 | 2/2013 | Uhle et al. | |
| 2013/0216055 A1 | 8/2013 | Wanca | |
| 2015/0016613 A1 | 1/2015 | Atwater et al. | |

OTHER PUBLICATIONS

International Search Report for PCT/US2020/017788 dated Apr. 29, 2020, 11 pages.
U.S. Appl. No. 11/251,051, US 2007-0084473 A, filed Apr. 19, 2007, Issued.
U.S. Appl. No. 15/857,065, US 2019/0201658 A1, filed Jul. 4, 2019, Issued.
U.S. Appl. No. 17/505,453, filed Oct. 19, 2021, Pending.
U.S. Appl. No. 17/366,896, filed Jul. 2, 2021, Pending.

*Primary Examiner* — Hien N Nguyen
(74) *Attorney, Agent, or Firm* — DLA Piper LLP (US)

(57) ABSTRACT

First data comprising a first range of audio frequencies is received. The first range of audio frequencies corresponds to a predetermined cochlear region of a listener. Second data comprising a second range of audio frequencies is also received. Third data comprising a first modulated range of audio frequencies is acquired. The third data is acquired by modulating the first range of audio frequencies according to a stimulation protocol that is configured to provide neural stimulation of a brain of the listener. The second data and the third data are arranged to generate an audio composition from the second data and the third data.

18 Claims, 14 Drawing Sheets

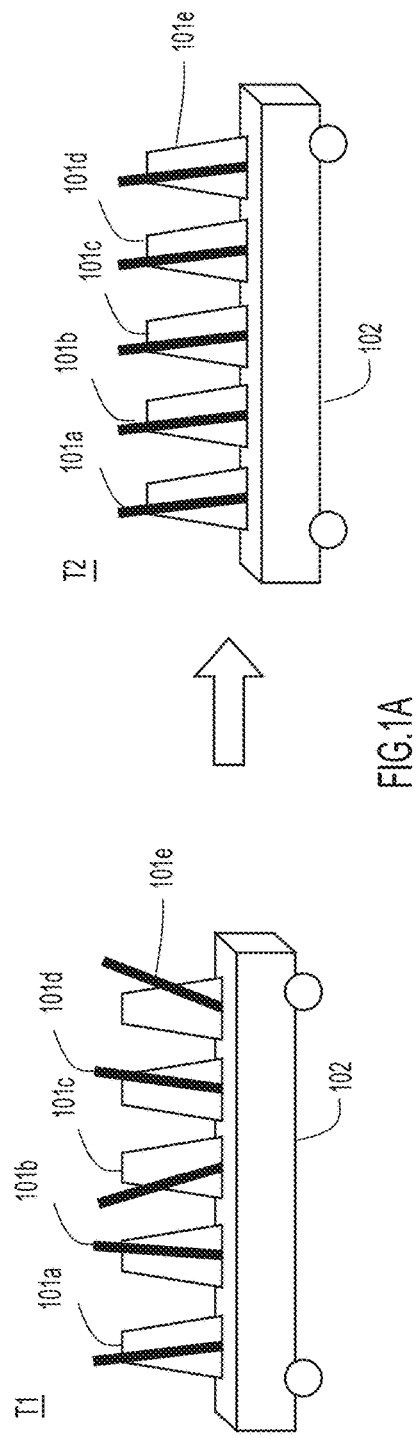
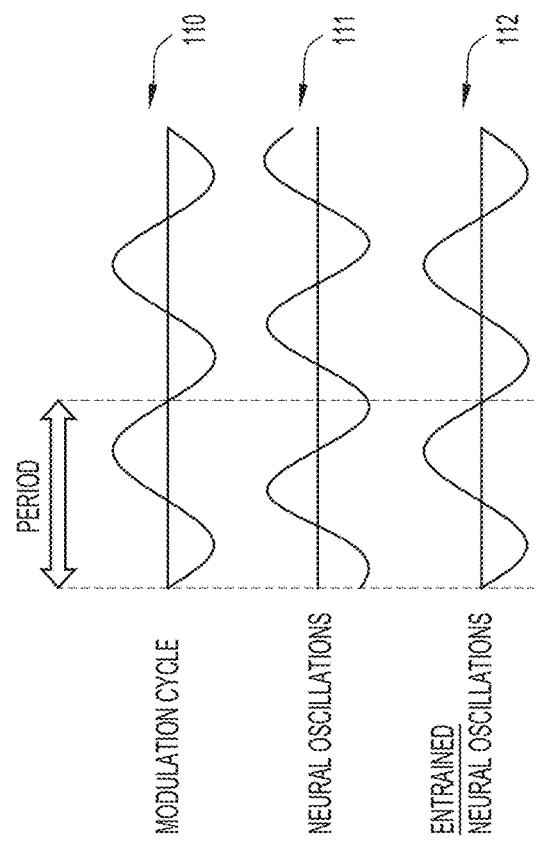

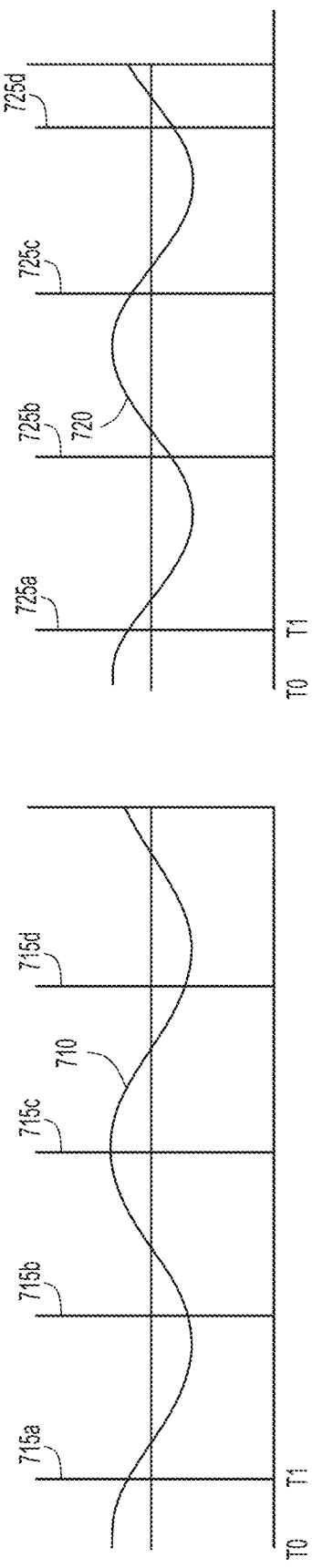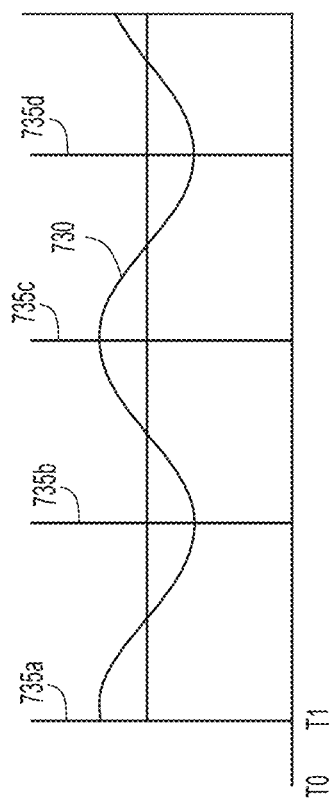

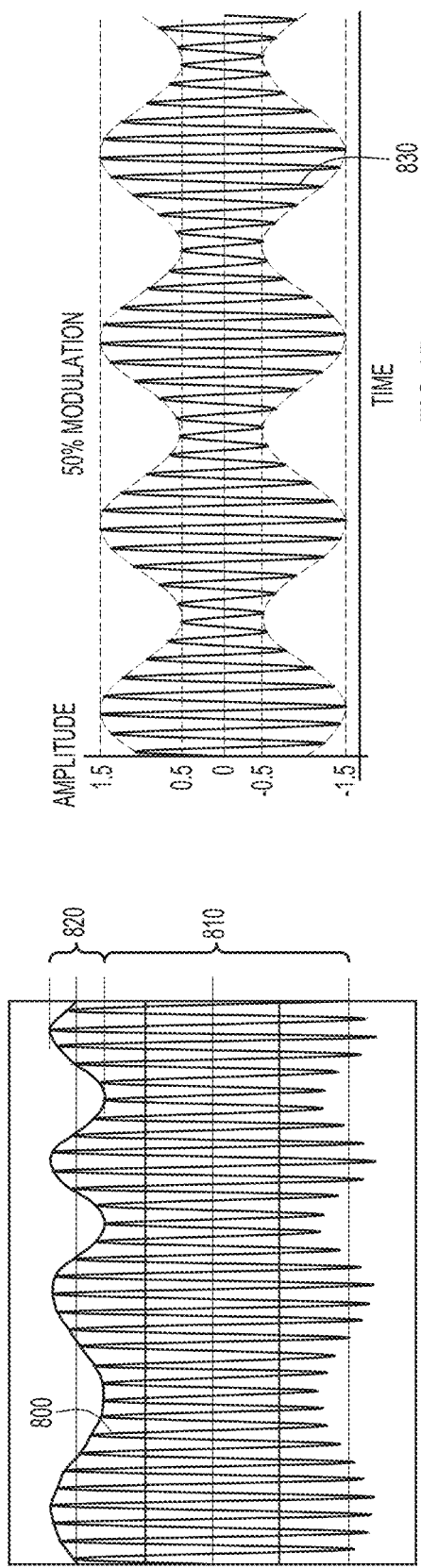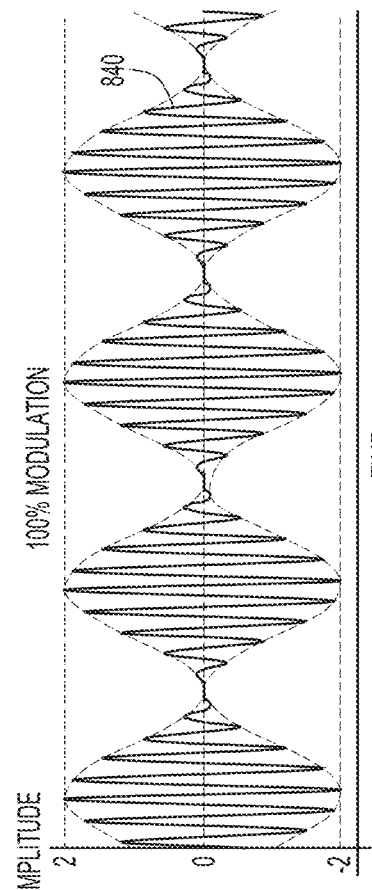

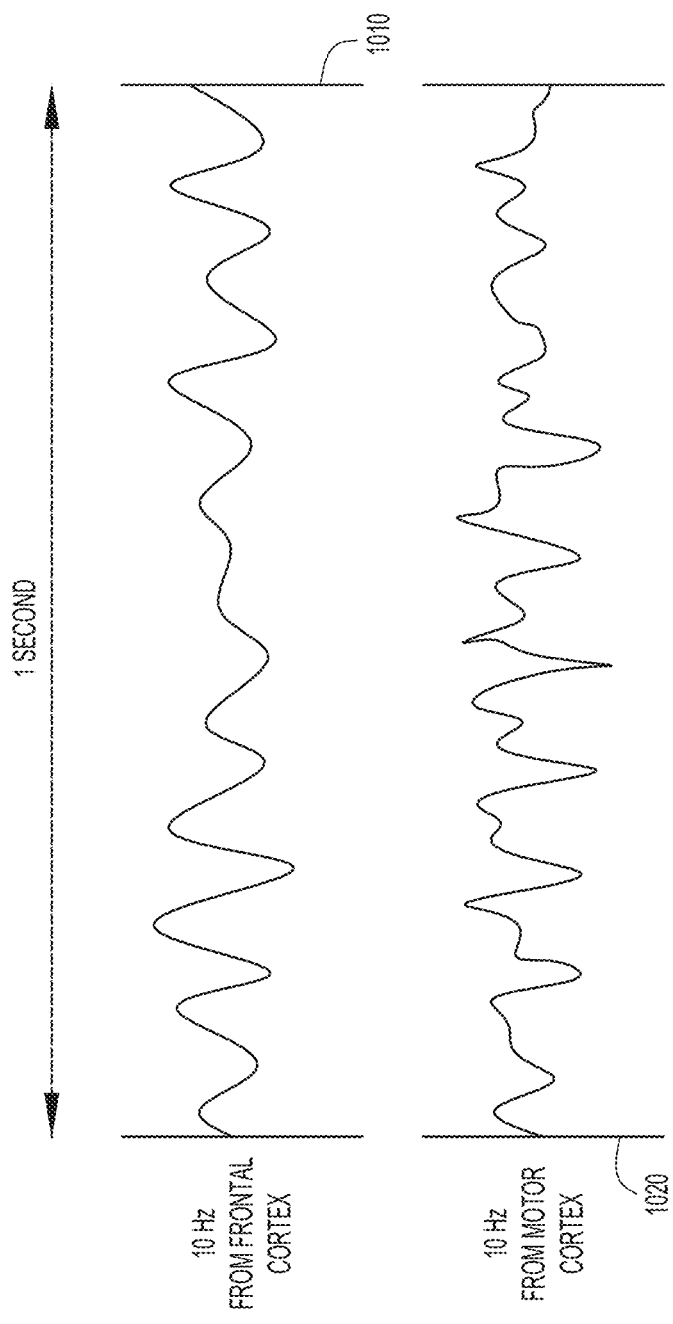
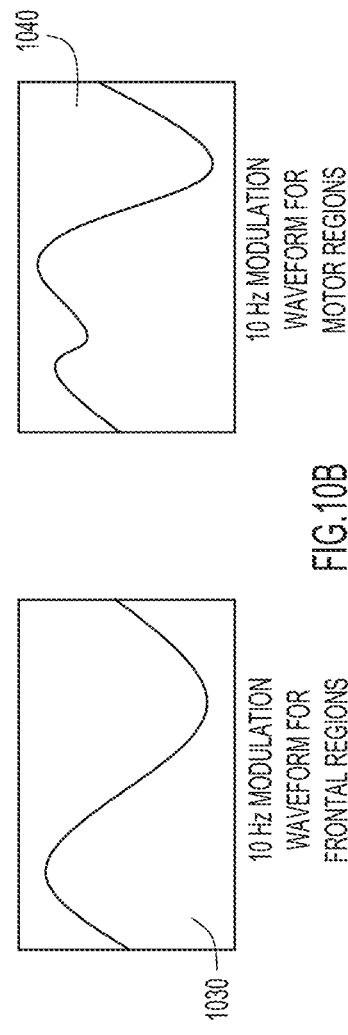

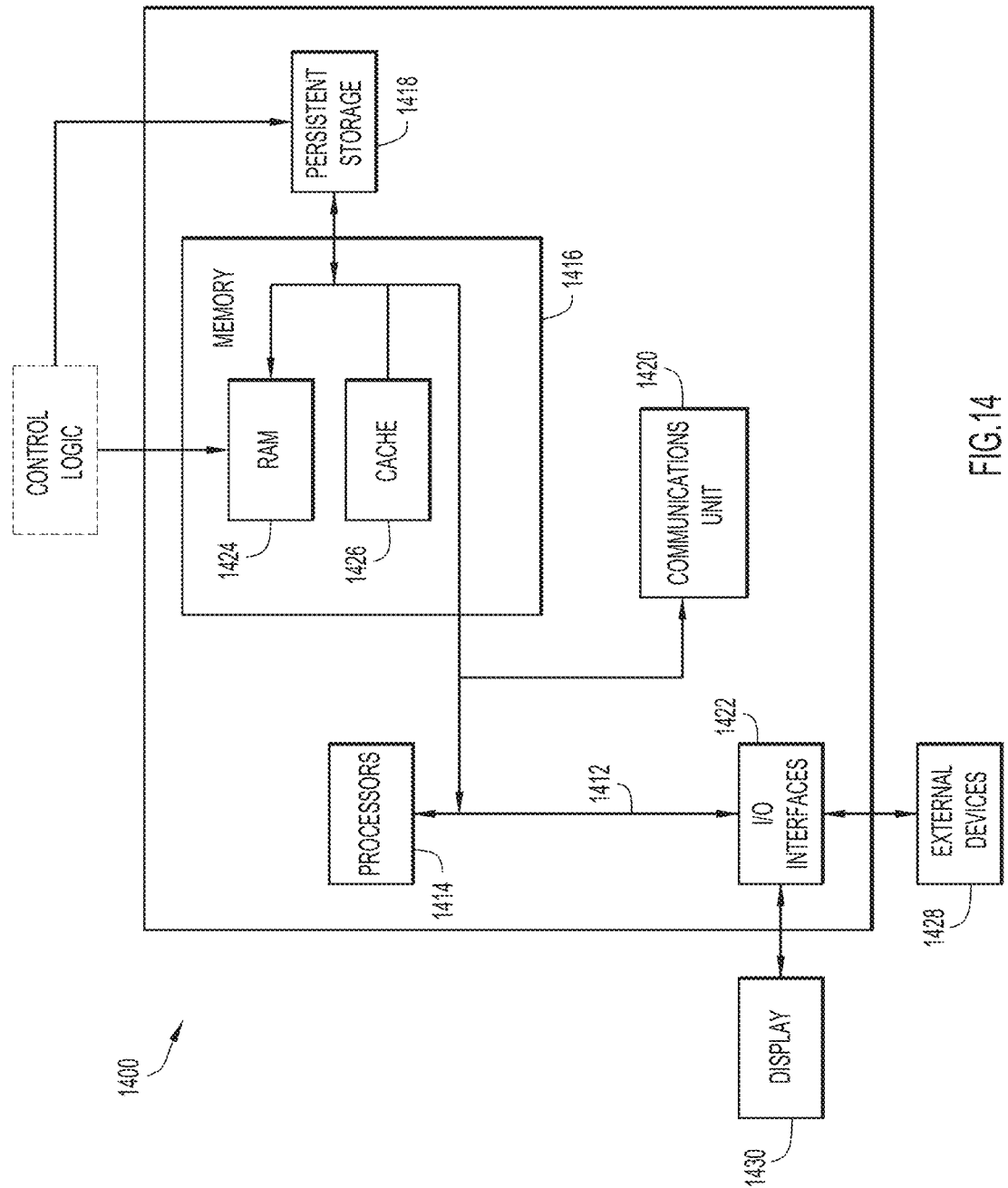

NONINVASIVE NEURAL STIMULATION THROUGH AUDIO

TECHNICAL FIELD

The present disclosure relates to neural stimulation, and in particular, noninvasive neural stimulation using audio.

BACKGROUND

For decades, neuroscientists have observed wave-like activity in the brain called neural oscillations. Various aspects of these oscillations have been related to attentional states. The ability to influence attentional states, via noninvasive brain stimulation, would be greatly desirable.

BRIEF DESCRIPTION OF THE DRAWINGS

FIGS. 1A and 1B are visual representations of entrainment, according example embodiments.

FIGS. 7A-C are visual representations of the alignment of a modulation signal with the rhythmic elements of an audio element being modulated according to phase and rate to provide noninvasive neural stimulation using audio, according to example embodiments.

FIGS. 8A-C are visual representations of modulation depth for use in noninvasive neural stimulation using audio, according to example embodiments.

FIGS. 10A and 10B are illustrations of modulation waveforms used to target specific areas of the brain for use in noninvasive neural stimulation using audio, according to example embodiments.

FIG. 14 is a functional diagram of an apparatus configured to provide the noninvasive neural stimulation using audio of the present disclosure, according to example embodiments.

DESCRIPTION OF EXAMPLE EMBODIMENTS

Overview

Figure 2:
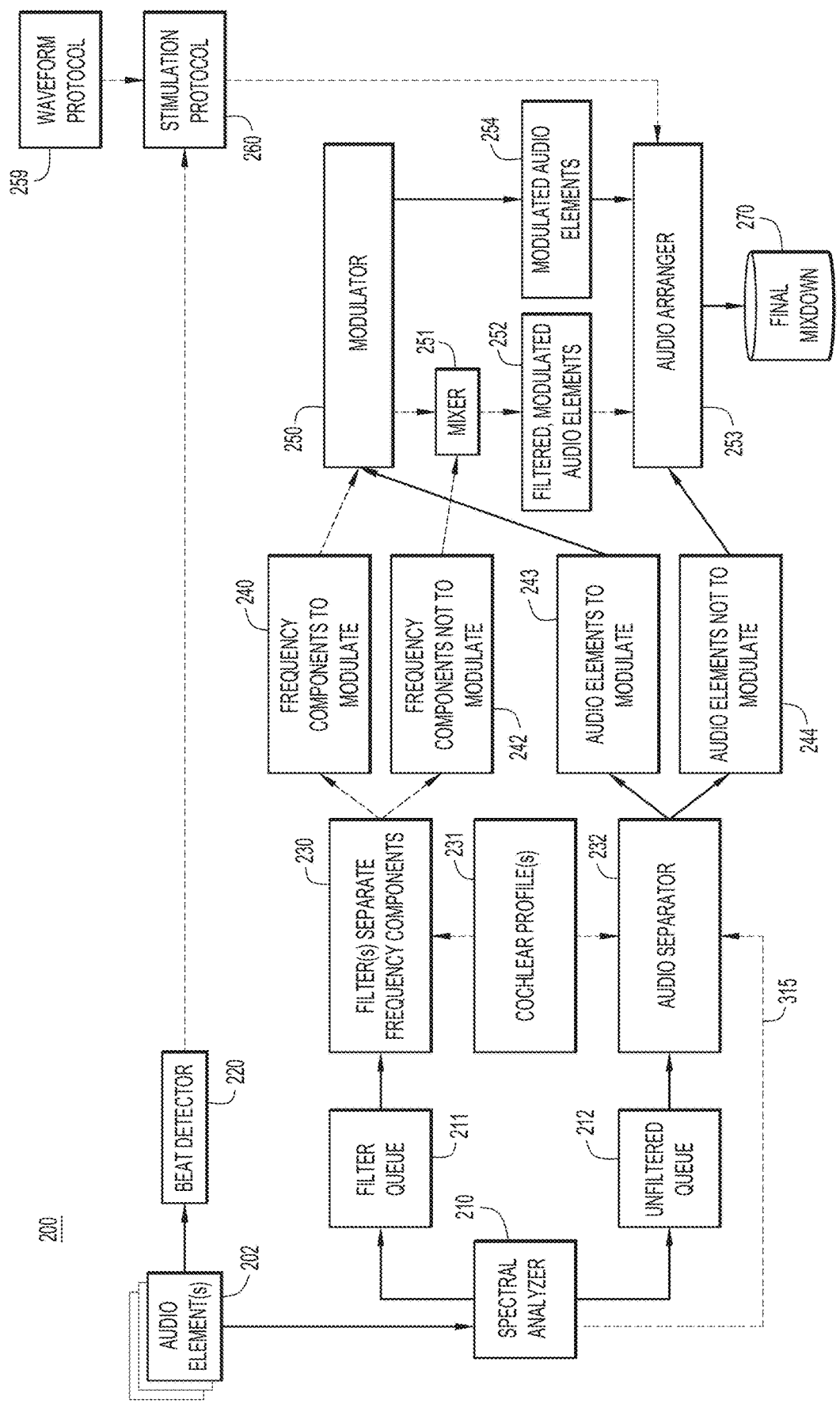
FIG. 2 is a process flow for providing noninvasive neural stimulation using audio, according to example embodiments.

The present disclosure is directed to methods of neural stimulation with any audio. Example embodiments provide a neuroscience-informed way to select for audio components which, when combined with modulated audio components, create an audio arrangement which will stimulate the brain in a noninvasive way.

According to example embodiments of the present application, first data comprising a first range of audio frequencies is received. The first range of audio frequencies corresponds to a predetermined cochlear region of a listener. Second data comprising a second range of audio frequencies is also received. Third data comprising a first modulated range of audio frequencies is acquired. The third data is acquired by modulating the first range of audio frequencies according to a stimulation protocol that is configured to provide neural stimulation of a brain of the listener. The second data and the third data are arranged to generate an audio composition from the second data and the third data.

Example Embodiments

Described herein are techniques that provide for noninvasive neural stimulation of the brain. For example, the techniques of the present application utilize modulation of audio elements (e.g., amplitude modulation or volume modulation) to provide stimulus to stimulate the brain. The concept behind this stimulation may be analogized to the way in which unsynchronized metronomes arranged on a table will synchronize due to constructive and destructive interference of the energy transferred between the metronomes via the platform on which they are arranged.

As illustrated in FIG. 1A, several metronomes 101a-e begin unsynchronized at a time T1. Energy is transferred between metronomes 102a-e via table 102. The metronomes 101a-e will reach a minimum energy state, as illustrated in time T2, characterized in the synchronization of the motion of metronomes 102a-e. This synchronization is analogous to how periodic and temporally structured sounds can synchronize and entrain the communication between neurons of the brain. External traveling waves (e.g., acoustic or audio waves) are converted to neuro-electric signals (e.g., via the ear), which entrain desired neural excitations within the brain. In other words, periodic audio may be used to entrain the attentional oscillatory cycles of the brain. Such neural stimulation may be used to improve a user's focus, memory, meditation and sleep, among others.

FIG. 1B depicts a simplified illustration of synchronization of external signals and neural oscillations. External modulated sound 110 is presented to the listener. The listener's existing neural oscillations 111 become synchronized, or entrained to match the external signals as illustrated in entrained neural oscillations 112. Specifically, the phase of neural oscillations 111 has shifted to match that of external signal 110, as illustrated in entrained neural oscillations 112.

The present disclosure provides methods, apparatuses and computer executable media configured to provide such neural stimulation via audio elements. As used herein, "audio element" refers to a single audio input, usually a single digital file, but also could be an audio feed from a live recording. As further explained below, the techniques may be particularly effective when the audio stimulation is provided by predetermined frequencies that are associated with known portions of the cochlea of the human ear. Furthermore, the techniques of the present application provide for the selection of the waveforms configured to target specific areas of the brain.

With reference now made to FIG. 2, depicted therein is a process flow 200 according to the techniques described herein. The process flow 200 is exemplary, and elements may be added or removed from process flow 200 without deviating from the inventive concepts of the present application. Process flow 200 is configured to generate a stimulation protocol 260. As used herein, a "stimulation protocol" (such as stimulation protocol 260) is one or more values that determine how a modulator (such as modulator 250) modulates audio frequency data to induce neural stimulation or entrainment. According to specific example embodiments, a stimulation protocol (such as stimulation protocol 260) may provide one or more of a modulation rate, phase, depth and/or waveform for the modulation to be applied to audio frequency data that is used to induce neural stimulation or entrainment. Modulation rate, phase, depth and waveform refer to four non-exclusive parameters used to control any low frequency oscillator. Rate is the speed of the oscillation, often defined in hertz. Phase is the particular point in the full cycle of modulation, often measured as an angle in degrees. Depth is the how large or small the modulation cycle is, in comparison to what it is modulating. In amplitude modulation, it would be expressed as a linear percent of the whole volume available. Waveform expresses the shape of the modulation cycle, such as a sine wave, a triangle wave or some other custom wave. Neural stimulation via such a stimulation protocol may be used on conjunction with a cochlear profile to induce effective stimulations in a user's brain.

The process flow 200 of FIG. 2 also provides for the generation of a cochlear profile for use in noninvasive neural stimulation. A cochlear profile refers to a list of frequency bands to be modulated generated based upon the portion of the human cochlea associated with the indicated frequency ranges. In other words, the cochlear profile refers a list of frequency bands to be modulated that correspond to one or more frequencies within the human auditory range. Frequencies not specified will be excluded from modulation. The process flow of FIG. 2 also illustrates the application of the stimulation protocol and the cochlear profile to provide neural stimulation.

The process flow 200 begins with an audio element or elements 202. An audio element 202 may be embodied as a live recording, pre-composed music files, audio with no music at all, or a combination of elements from all three. To achieve better brain stimulation, a wide spectrum of sound may be used, as opposed to just a single tone or a several tones. Accordingly, audio elements 202 may be selected such that the combination of audio elements have a large spectral audio profile—in other words, audio elements 202 are selected such that the combination of the audio elements has many frequency components. For example, one or more of audio elements 202 may be selected from music composed from many instruments with timbre that produces overtones all across the spectral profile.

Furthermore, the audio elements 202 may be selected to ensure both a large number of frequencies are being modulated, and also ensuring that unmodulated frequency regions are also included so that a listener is not disturbed by the modulations giving rise to the brain stimulations. For example, according to the techniques described herein, a band pass filter may be used to extract a frequency region, such as 400 Hz to 900 Hz, from an audio element, while a band stop filter may be used to generate a signal with all but the 400 Hz to 900 Hz frequency range. This extraction would result in one audio element file with only this frequency region and one audio element file without it. A "band pass filter" is a device or process that passes frequencies within a certain range and rejects frequencies outside that range, while a "band stop filter," also called a notch filter, t-notch filter, band-elimination filter, and band-rejection filter, is a conventional audio process that passes most frequencies unaltered, but attenuates those in a range to very low levels.

Figure 3:
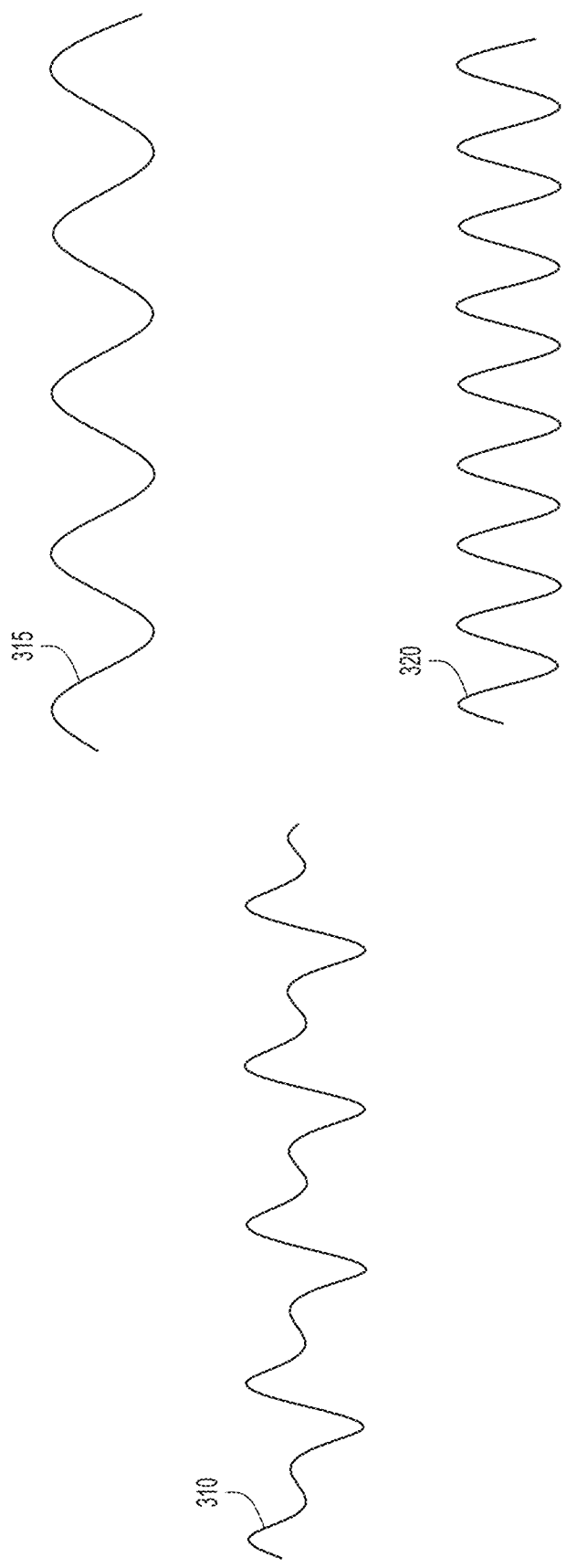
FIG. 3 is a visual representation of audio filtering used in providing noninvasive neural stimulation using audio, according to example embodiments.

Illustrated in FIG. 3 is a simplified example of such a filter processing. Audio element 310 comprises two frequency components, a first frequency component at a frequency of "X," and a second frequency component of "2X." After passing through a band pass filter that filters frequency "X," filtered audio element 315 is generated, comprising the "X" frequency component. After passing through a band notch filter configured to attenuate frequency "X," filtered audio element 320 is generated, which comprises the "2X" frequency component. Audio element 315 may be modulated to provide brain stimulation or entrainment, while audio element 320 would remain unmodulated. The two audio elements could be combined to create a cohesive experience not unlike the original save for the additional modulations. Such an audio element may then be used to provide neural stimulation and entrainment in such a way that a listener is not disturbed by the modulations giving rise to the brain stimulations. Real world audio elements may comprise a wide range of frequencies, and the band pass filter may extract a range of frequency values, while the band stop filter would attenuate a range of frequency values. The simplified audio elements of FIG. 3 were chosen to illustrate the effect of a filtering process as used in the present example embodiment with an easily visualized audio element. In fact, to achieve the best possible brain stimulation, a wide spectrum of sound may be used, as opposed to just a single tone or a several tones. Furthermore, the stimulation may come from audio that has a large spectral audio profile—in other words, audio that has many frequency components, like music with its many instruments and timbre that produces overtones all across the spectral profile, as will be described in greater detail below.

Returning to FIG. 2, audio element 202 is provided to spectral analyzer 210. Spectral analyzer 210 analyzes the frequency components of audio elements 202. "Spectral analysis" refers to sonographic representations and mathematical analysis of sound spectra, or by mathematically generated spectra. "Spectral range" or "spectral region" refers to specific bands of frequencies within the spectra. As will be described in greater detail below, spectral analyzer 210 may be used to determine how the frequency components of audio element 202 are to be utilized to implement the non-invasive neural stimulation techniques of the present disclosure.

Specifically, spectral analyzer 210 analyzes the frequency components of each audio element 202. If it is determined that one or more of audio elements 202 are composed of a large variety of frequency components across the spectrum, the one or more audio elements 202 are sent to the filter queue 211. As its name implies, the filter queue 211 is a queue for audio filter 230. Because the stimulation protocol 260 may be applied to a specific frequency or a relatively narrow range of frequencies, audio elements 202 that contain a large variety of frequency components undergo filtering in operation 230 to separate these large varieties of frequency components. For example, audio elements that contain audio from a plurality of instruments may contain audio data with frequency components that cross the audible frequency spectrum. Because the stimulation protocol 260 will only be applied to a subset of these frequencies, such audio elements are sent to audio filter 230. In other words, the filtering of operation 230 selects a frequency range from an audio element for modulation.

If it is determined that one or more of audio elements 202 has a single frequency component, or multiple frequency components but centered around a narrow band, the one or more audio elements 202 are sent to unfiltered queue 212. In other words, if the audio element 260 covers a sufficiently narrow frequency range, the stimulation protocol 260 may be applied to the entire audio element, and therefore, no further filtering would be required. Accordingly, such audio elements are sent to audio separator 232. Audio separator 232 looks at the spectral data of an audio input and pairs it with a cochlear profile to determine if the audio input should be modulated or not.

Additionally, spectral data may be sent from spectral analyzer to one or more of audio filter 230 and audio separator 232. This spectral data may be used, for example, in conjunction with cochlear profile 231, to determine which portions of the audio elements 202 are to be modulated according to stimulation protocol 260.

Both audio filter 230 and audio separator 232 are configured to filter audio elements for modulation (in the case of filter 230) or select audio elements for modulation (in the case of selector 232) based upon one or more cochlear profiles 231. Cochlear profile 231 provides instructions to one or more of filters 230 and/or selector 232 based upon the frequency sensitivity of the cochlear of the human ear. According to the present example embodiment, "cochlear profile" refers to a list of frequency bands to be modulated. Frequencies not specified will be excluded from modulation.

Figure 4:
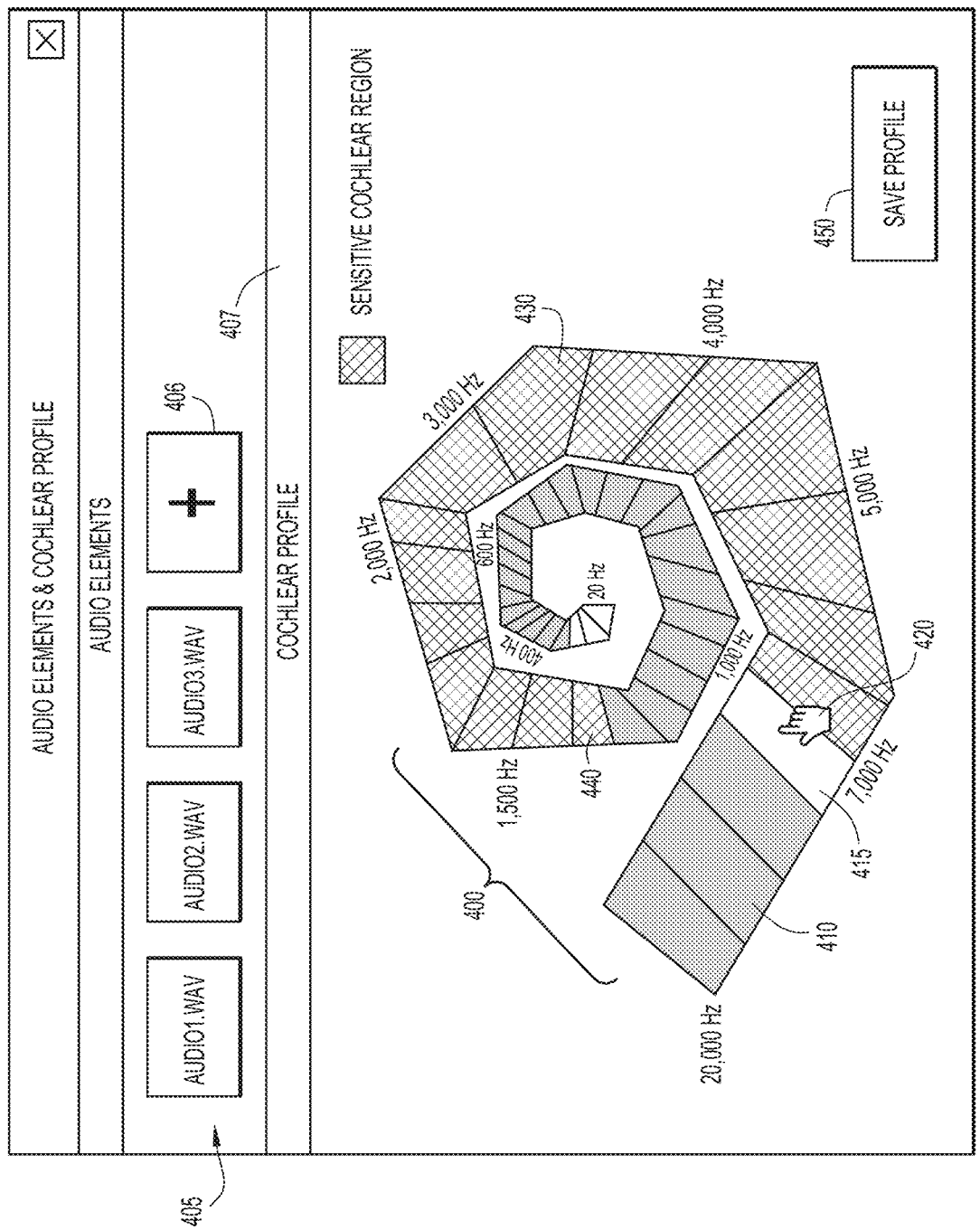
FIG. 4 is an illustration of a software user interface configured to generate a cochlear profile for use in noninvasive neural stimulation using audio, according to example embodiments.

With reference now made to FIG. 4, depicted therein is a visual representation of the cochlea 400 of the human ear. The cochlea 400 is the spiral cavity of the inner ear containing the organ of Corti, which produces nerve impulses in response to sound vibrations. Different portions of cochlea 400 sense sounds at different frequencies due to the shape and rigidity of the cochlea 400 in the different regions. The base of the cochlea 400, closest to the outer ear, is stiff and where higher frequency sounds are transduced. The apex, or top, of the cochlea is more flexible and transduces lower frequency sounds.

The cochlea, in addition to sensing different frequencies in different regions, also has sensitivity that varies with the region of the cochlea. Each region has a number of cochlear filters that help the brain decide what to pay attention to. Sensitive cochlear regions draw attention more than insensitive regions. For example, sound in the frequency range of a human scream will draw our attention where the same sound, reduced in pitch to bass level, may be completely overlooked. The difference in reaction is largely due to the sensitivity of different areas in the cochlea. Knowing how the cochlea and larger auditory system draw our attention enables neural stimulation to be incorporated into audio without disturbing the listener. Specifically, it has been determined that modulation targeting frequencies associated with the insensitive regions of the cochlea will stimulate the brain without disturbing the listener.

For example, by providing stimulation through the modulation of frequencies between 0 Hz-1500 Hz, the modulation may be less noticeable to the listener but the modulation may have a substantial stimulation effect on the brain. Providing modulation at frequencies higher than the 0 Hz-1500 Hz range may be avoided because the sensitivity of the cochlear regions increases dramatically for high frequencies. Similarly, the stimulation could be provided through modulation at frequencies between 8 kHz and 20 kHz, as the sensitivity of the cochlea decrease at such higher frequencies.

As a counter example, sensitive areas of the cochlea may be targeted specifically if the audio being modulated supports it without being obtrusive. For example, there are relatively insensitive regions of the cochlea between 5 kHz and 6.5 kHz, and these frequencies may be modulated in audio elements that lack significant audio components in this range. For example, audio elements created using instruments that do not make great use of that range may provide stimulation through modulation of this range.

According to other examples, audio elements created with instruments that make heavy use of a region within a usually insensitive band, such as 900-1200 Hz, may be used for brain stimulation. These special cases may be taken into account using spectral profiling, but generally avoiding highly sensitive regions is a safe, effective way to highly stimulate the brain without disturbing the listener.

As illustrated in FIG. 4, region 410, a region sensitive to particularly high frequency sounds, and region 440, a region sensitive to particularly low frequency sounds, are generally less sensitive than region 430, a region sensitive to intermediate frequency sounds.

It has been determined that neural stimulation targeting insensitive regions (i.e., stimulation protocols that modulate high and low frequency sounds) will stimulate the brain without disturbing the listener. For example, stimulation protocols associated with these relatively low sensitivity regions will achieve the entrainment described above with reference to FIG. 1. Yet, because the stimulation is implemented through frequencies to which the human ear is less sensitive, the stimulation may not affect the listener's enjoyment of, for example, music that contains audio elements substantially within the sensitive region 430.

Further, it has been determined that modulation of both low and high frequencies has a special effect on the brain. If both regions have identical modulation, the brain fuses the two regions into a single virtual source, increasing the fidelity of the stimulation waveform. Therefore, by avoiding sensitive cochlear regions while targeting both high and low regions, the fidelity of the stimulation waveform may be increased without disturbing the listener. For example, a piece of audio could be modulated using frequencies between 0-1500 Hz and frequencies between 8 kHz-20 kHz. The modulation of the two frequency regions may be substantially identical in waveform, phase and rate. Such modulation may create increased waveform fidelity for both ranges of stimulation.

Figure 5:
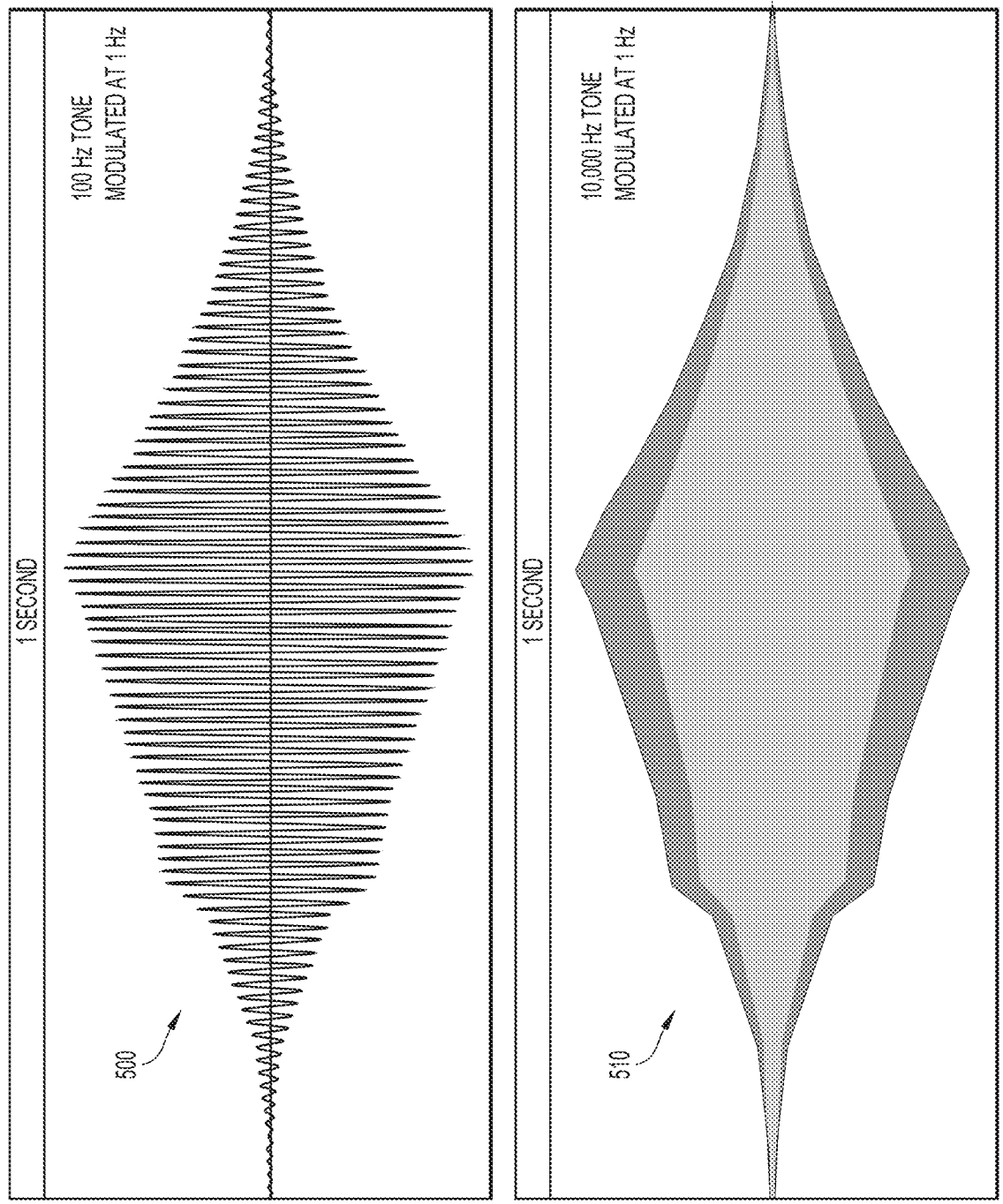
FIG. 5 is a visual representation of audio fidelity for use in noninvasive neural stimulation using audio, according to example embodiments.

Fidelity of the waveform is analogous to the difference in resolution of digital images: a low resolution image has less pixels, and thus will not be able to capture as much detail as a high resolution image with more pixels. In the same way, high frequency carriers are able to increase the fidelity of a modulation waveform. Depicted in FIG. 5 is an audio analysis of amplitude modulation applied to a carrier of 100 Hz (210) where the waveform shape of the modulation is not clearly recreated when compared to a modulated carrier of 10,000 Hz (210), which looks smooth due to its higher fidelity.

The fidelity of the stimulation waveform may have a significant impact on the effectiveness of the neural stimulation provided by the modulation. Just as in audio synthesis, neural oscillations will react differently depending on the waveform of the modulation.

Returning to FIG. 4, the visual representation of the cochlea 400 is implemented through a software interface that may be used to select cochlear regions to target for stimulation, in which cochlear regions represent frequency bands across the spectrum of human hearing. The software interface of FIG. 4 would be used to create a cochlear profile to be used in filters and audio separators. For example, a user input device 420 may be used to select portions of the cochlea 400 associated with the frequency ranges that the user determines should be stimulated via the stimulation protocol. According to the example of FIG. 4, the user input device 420 has been used to select cochlear region 415 associated with 7,000 Hz-8,500 Hz. Accordingly, the cochlear profile 231 of FIG. 2, may instruct both the audio filter 230 and the audio separator 332 to select 7,000 Hz-8,500 Hz as a frequency range to receive modulation per the stimulation protocol. 260. The software interface of FIG. 4 may also be used to add audio elements 406 to the project, and assign audio elements 405 to the cochlear profile 407.

Returning to FIG. 2, each audio element in filter queue 211 may be filtered via audio filter 230, and based upon the frequency range filtered by audio filter 230, the frequency data may be sent to modulator 250 for modulation according to stimulation protocol 260, or sent to mixer 251 for recombination with the modulated components for inclusion in a final audio element.

For example, audio filter 230 may receive instructions from the cochlear profile 231 for each audio element being filtered. These instructions may indicate which frequency range within the audio element are to be modulated, for example the frequencies corresponding to the less sensitive portions of the human cochlea. In carrying out this operation, audio filter 230 may use one or more band passes to extract the chosen frequency components for modulation 240. Accordingly to other example embodiments, band stop filters, equalizers, or other audio processing elements known to the skilled artisan may be used in conjunction with or as an alternative to the band pass filter to separate the contents of filter queue 211 into frequency components for modulation 240 and frequency components that will not receive modulation 242.

The frequency components for modulation 240 are passed to modulator 250 in accordance with the frequencies indicated in cochlear profiles 231. The remainder of the frequency components 242 are passed directly to the mixer 251 where modulated and unmodulated frequency components are recombined to form a single audio element 252. This process is done for each audio element in the filter queue 211.

Similarly, audio separator 232 may receive instructions from the cochlear profile 231 selected for each audio element. Based upon the instructions provided by cochlear profile 231, audio separator 232 may separate the audio elements contained in unfiltered queue 212 into audio elements to be modulated 243 and audio elements not to be modulated 244. By placing an audio element into audio elements to modulate 243, audio separator 232 selects a frequency range comprising the entirety of the audio element for modulation. Accordingly, the audio elements to be modulated 243 are sent to modulator 250, while the audio elements not to be modulated are sent to audio arranger 253, where these audio elements will be arranged with audio elements that contain modulation to form a final combined audio element.

As illustrated in FIG. 2, modulator 250 applies stimulation protocol 260 to the frequency components for modulation 240 and the audio elements to be modulated 243. The stimulation protocol 260 specifies the duration of the auditory stimulation, as well as the desired stimulation across that timeframe. To control the stimulation, it continually instructs modulator 250 as to the rate, depth, waveform and phase of the modulations.

Figure 6:
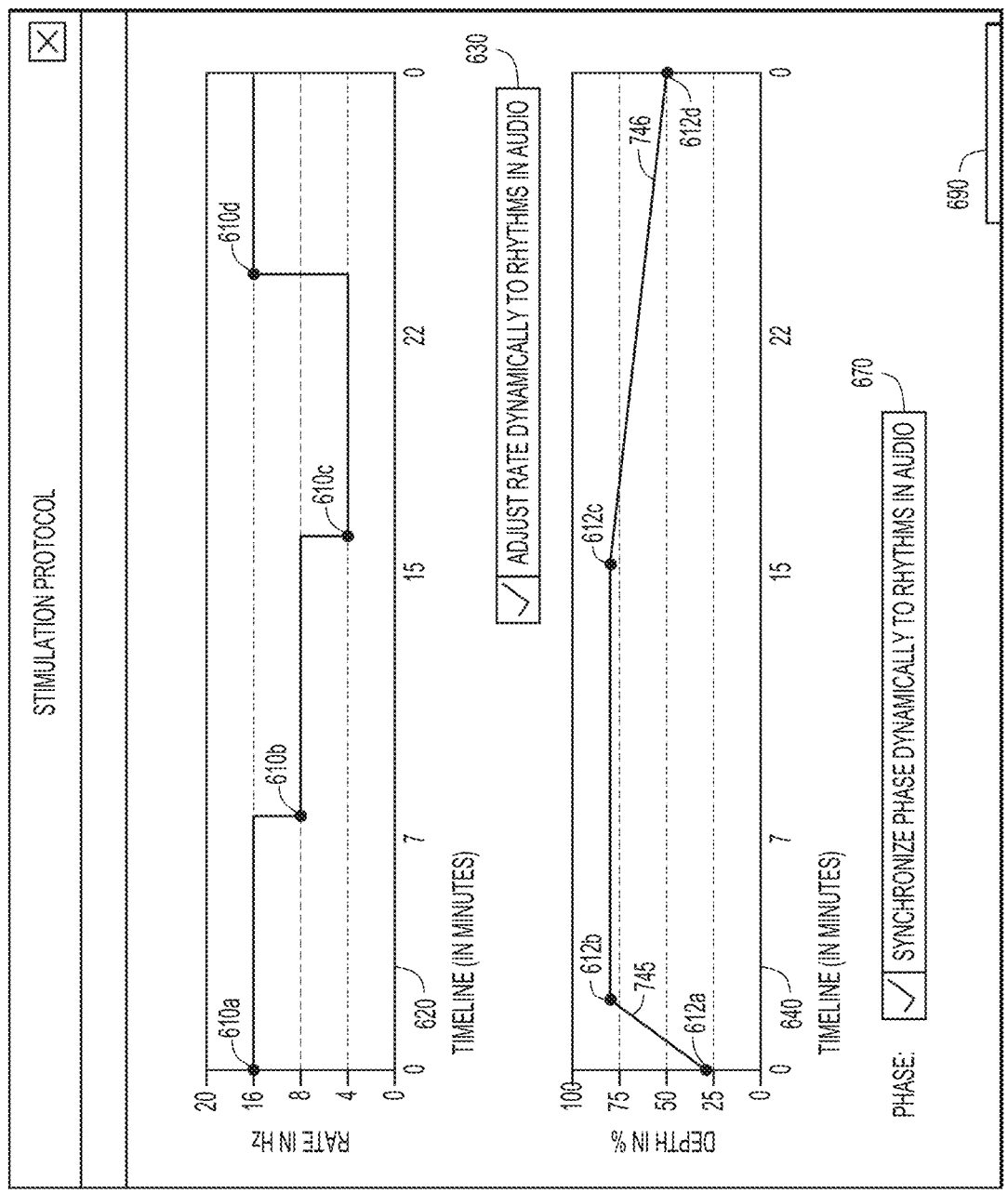
FIG. 6 is an illustration of a software user interface configured to generate a stimulation profile for use in noninvasive neural stimulation using audio, according to example embodiments.

Turning to FIG. 6, illustrated therein is an example of a stimulation protocol according to the techniques described herein. In particular, FIG. 6 illustrates a software interface 600 that may be utilized to create a stimulation protocol to provide neural stimulation. Specifically, the stimulation protocol illustrated in FIG. 6 includes controls for the rate of the stimulation 620, and the depth of the stimulation 640. According to the example of FIG. 6, these features of the stimulation protocol are defined as a function of time.

The rate of the stimulation 620 may be established such that the modulation provided by the stimulation protocol synchronizes amplitude modulation of the audio elements being modulated to rhythms in the underlying audio elements. The stimulation protocol may adjust the modulation phase to align with rhythmic acoustic events in the audio. By aligning the modulation with the acoustic events in the audio elements being modulated, the stimulation protocol may be generated to ensure that the stimulation provided by the modulator is not interfered with by the underlying audio elements being modulated, and vice versa, keeps the stimulating modulation from interfering with the underlying music. Rhythmic acoustic events such as drum beats in music, or waves in a beach recording, are perceived in the brain as a form of amplitude modulation. If the modulation provided by the stimulation protocol is not aligned with these rhythmic acoustic events of the audio elements being modulated, the rhythmic acoustic events could interfere with the stimulation modulation. This misalignment would create interference between the rhythmic elements of the audio elements and the amplitude modulations meant to stimulate the brain. Accordingly, it may be beneficial to synchronize the stimulation protocol modulation with the rhythmic elements of the audio element being modulated.

Furthermore, synchronizing the stimulation protocol modulation with the rhythmic elements of the audio element being modulated prevents distortion of the audio by allowing the modulation cycle crest to align with the crest of notes or beats in music. For example, music at 120 beats per minute equates to 2 beats a second, equivalent to 2 Hz modulation. Quarter notes would align with 2 Hz modulation if the phase is correct. 8th notes would align at 4 Hz, 32nd notes would align with 16 Hz. If a stimulation protocol is being applied to music in an MP3 which plays at 120 beats per minute (BPM), the stimulation protocol would want to modulate the audio elements of the music file at 2 Hz. Specifically, "hertz" refers to a number of cycles per second, so 2 Hz corresponds to 120 BPM, as a 120 BPM piece or music will have two beats every second. Similarly, the rate of modulation may be set as a multiple of BPM for the audio element.

Illustrated in FIGS. 7A-C are visual representations of modulations that are not aligned with the beats of an audio element (FIG. 7A), modulations whose rate, but not phase, is aligned with the beats of an audio element (FIG. 7B), and modulations whose rate and phase are aligned with the beats of an audio element (FIG. 7C).

The frequency of modulation signal 710 of FIG. 7A is not a multiple of the frequency of beats 715a-d, and therefore, the maxima of signal 710 cannot be aligned with beats 715a-d. In other words, signal 710 has a different rate than the rhythmic components illustrated through beats 715a-d. Similarly, because modulation signal 710 begins at time T0 and the rhythmic components of the audio element do not start until time T1, modulation signal 710 would be out of phase with beats 715a-d even if its rates were the same. The frequency of modulation signal 720 of FIG. 7B is a multiple of the frequency of beats 725a-d, but because the modulation signal 720 begins at time T0 and the rhythmic components of the audio element do not start until time T1, modulation signal 720 is out of phase with beats 725a-d. The frequency of modulation signal 730 of FIG. 7B is aligned with the frequency of beats 735a-d, and this alignment is accomplished by phase shifting the modulation signal 720 such that modulation signal 730 begins at T1, instead of at time T0.

In order to ensure that the stimulation protocol aligns with the rhythmic elements of the audio elements being modulated, the phases of the stimulation modulation and the rhythmic elements of the audio element may be aligned. Returning to the example of the 120 BPM MP3 file, applying 2 Hz modulation to the MP3 file may not align with the rhythmic elements of the MP3 file if the phase of the stimulation modulation is not aligned with MP3 file. For example, if the maxima of the stimulation modulation is not aligned with the drum beats in the MP3 file, the drum beats would interfere with the stimulation modulation, and the stimulation protocol may cause audio distortion even through the stimulation modulation is being applied with a frequency that matches the rate of a 2 BPM audio element.

Such distortion may be introduced because, for example, MP3 encoding often adds silence to the beginning of the encoded audio file. Accordingly, the encoded music would start later than beginning of the audio file. If the encoded music begins 250 milliseconds after the beginning of the encoded MP3 file, stimulation modulation that is applied at 2 Hz starting at the very beginning of the MP3 file will be 180° out of phase with the rhythmic components of the MP3 file. In order to synchronize the modulations to the beats in the file, the phase of the modulation would have to be shifted by 180°. If the phase of the modulation is adjusted by 180°, the modulation cycle will synchronize with the first beat of the encoded music.

In order to ensure that the stimulation modulation aligns with the rhythmic elements of the audio elements being modulated, the audio elements are provided to a beat detector, an example of which is illustrated as beat detector 220 of FIG. 2. "Beat Detection" refers to a process of analyzing audio to determine the presence of rhythms and their parameters, such that one can align the rhythms of one piece of audio with the rhythms of another. Accordingly, beat detector 220 detects rhythms in music or rhythmic auditory events in non-music audio. Beat detector 220 detects the phase and rate of the rhythms. Rhythmic information may already be known about audio element 202 through, for example, metadata included in audio element 202. This rhythmic information may indicate the phase where the rhythm of the audio element begins (e.g., at a particular phase) or that the rhythmic element has a defined rhythm rate (e.g., defined in BPM of the audio element). Beat detector 220 may be configured to read or interpret this data included in audio element 202.

According to other example embodiments, rhythm detector 220 may be configured to analyze the content of audio elements to determine information such as the phase and BPM of audio element 202. For example, according to one specific example embodiment, five musical pieces would be selected, and each musical piece would be a WAV file, six minutes long. Beat detector 220 may determine that each of the musical pieces has a BPM of 120. Beat detector 220 may further determine that each musical piece starts immediately, and therefore, each musical piece has a starting phase of 0. According to other examples, beat detector 220 may determine that each musical piece has a silent portion prior to the start of the musical piece, such as the 250 millisecond delay provided by some MP3 encoding. Beat detector 220 may detect this delay, and convert the time delay into a phase shift of the rhythmic elements of the music based upon the BPM of the musical piece. As illustrated in FIG. 2, the data determined by beat detector 220 is provided to stimulation protocol 260. This data may be used to ensure that the modulation provided by the stimulation protocol aligns with the rhythmic elements of the audio elements being modulated.

Returning to FIG. 6, the modulation rate 620 may be set to 16 Hz (corresponding to 32nd notes of a 120 BPM audio element) for the first 8 minutes of the audio element, 8 Hz (corresponding to 16th notes of a 120 BPM audio element) for the next 8 minutes, 4 Hz (corresponding to 8th notes of a 120 BPM audio element) for the next 8 minutes and once again to 16 Hz for the final 6 minutes of the audio element. As illustrated in element 630, the rate of the stimulation protocol may be dynamically adjusted to mate the rhythmic elements of the audio elements being modulated by the stimulation protocol based upon the data provided by, for example, beat detector 220 of FIG. 2. Similarly, the phase of the modulation may be dynamically mated to the rhythms in the audio via checkbox 630. The rate 620 may also specified across the duration of the stimulation by moving points 610a-d via user input.

As also illustrated in FIG. 6, the depth of the stimulation 640 may also be controlled. Modulation depth refers to the intensity of the modulation applied to the audio element. In other words, depth is the how large or small the modulation cycle is in comparison to what it is modulating. In amplitude modulation, depth would be expressed as a linear percent of the whole volume available.

The concept of modulation depth is illustrated in FIGS. 8A-C. Illustrated in FIG. 8A is an amplitude modulated signal 800. Value 810 is the unmodulated peak to peak carrier amplitude, while value 820 is the peak-to-peak audio amplitude after modulation. The percentage of modulation depth is the ratio of the peak-to-peak audio amplitude after modulation 820 to the peak to peak audio amplitude of the unmodulated signal. FIG. 8B illustrates a signal 830 with 50% modulation depth. According to this specific example embodiment, a modulation depth of 50% means that the modulation is causing 50% of the volume of the audio element to rise and fall periodically throughout the audio element. FIG. 8C illustrates a signal 840 with 100% modulation depth. According to this specific example embodiment, a modulation depth of 100% means that the modulation is causing 100% of the volume of the audio element to rise and fall periodically throughout the audio element.

Returning to FIG. 6, it has been demonstrated that high depth modulation produces greater neural stimulation. High intensity neural stimulation of this type has the advantage of producing better behavioral results in a short period, such as 15 minutes, but can have disadvantages past that time. In the same way that too much coffee can make one jittery, high intensity neural stimulation for too long can actually decrease performance. Therefore, it may be beneficial to moderate the depth of modulation across the stimulation timeline. For example, in a 30 minute stimulation session, one might modulate at a high depth of 70% for a first portion of the audio element. However, at the 15 minute mark, the modulation depth may be gradually reduced such that the modulation depth is down to 50% by the end of the audio element. This would effectively have the advantage of both high intensity stimulation and a "cool down" period where the user would be less stimulated and so maintain peak performance. Such a stimulation session is illustrated in depth of stimulation 640. As illustrated, the depth of modulation period 645 increases from 25% to 75% to allow the listener some time to adjust to the modulation. After this "ramp up" period, there is an extended period with 75% modulation depth to ensure a high level of neural stimulation. This period of high depth modulation may comprise a majority of the audio piece to which modulation has been applied. Period 645 may increase the depth of the modulation over a period with a minimum length 15 seconds. Additionally, modulation depth gradually decreases from 75% to 50% over the last 15 minutes of the audio element to prevent overstimulation. Accordingly to other example embodiment, this decrease in depth takes place of over a minimum length of time of one minute. Accordingly to still other example embodiments, the modulation depth may continually change from high to low and back again, with a minimum of 15 seconds between high and low phases.

The depth 640 may also specified across the duration of the stimulation by moving points 612a-d via user input. Finally, a save button 690 is provided to save the protocol to an electronic medium.

Returning again to FIG. 2, as illustrated therein, stimulation protocol 260 is based upon data provided by beat detector 220, and also waveform protocol 259. Waveform protocol 259 may be used to effect neural oscillatory overtones and/or to target specific brain regions by specifying the waveform of the modulation pattern applied to the audio elements being modulated. Neural oscillations may react differently depending on the waveform of the modulation. Sine waveform modulation may be used if stimulation is intended to target a single frequency of neural oscillations. As a sine waveform has no overtones included in the waveform, sine wave modulation waveforms may produce few overtones in the brain. More complex waveforms may be used to produce neural oscillatory overtones. "Overtones" or "harmonics" refer to resonant frequencies above the fundamental frequency that are produced when the waveform of an oscillator is anything other than a sine wave. An example of a waveform that contains overtones is illustrated in FIG. 3. Waveform 310 includes a fundamental frequency "X" and an overtone or harmonic "2X." Each of waveforms 315 and 320 contains just a sine waveform, and therefore, just contains its respective fundamental frequency.

In music, overtones contribute to timbre—the way a piano and a guitar, playing the same fundamental frequency, will sound completely different from one another. Brain imaging data has also shown that complex waveforms delivered with waveforms that contain overtones result in broader stimulation of neural oscillatory overtones far past the range of stimulation. Accordingly, "neural oscillatory overtones" refer to resonant frequencies above the fundamental frequency of stimulation. Like audio, or any data with a time-series, neural oscillations show harmonic and overtone frequencies when analyzing the spectrum and the fundamental frequency of stimulation.

Figure 9:
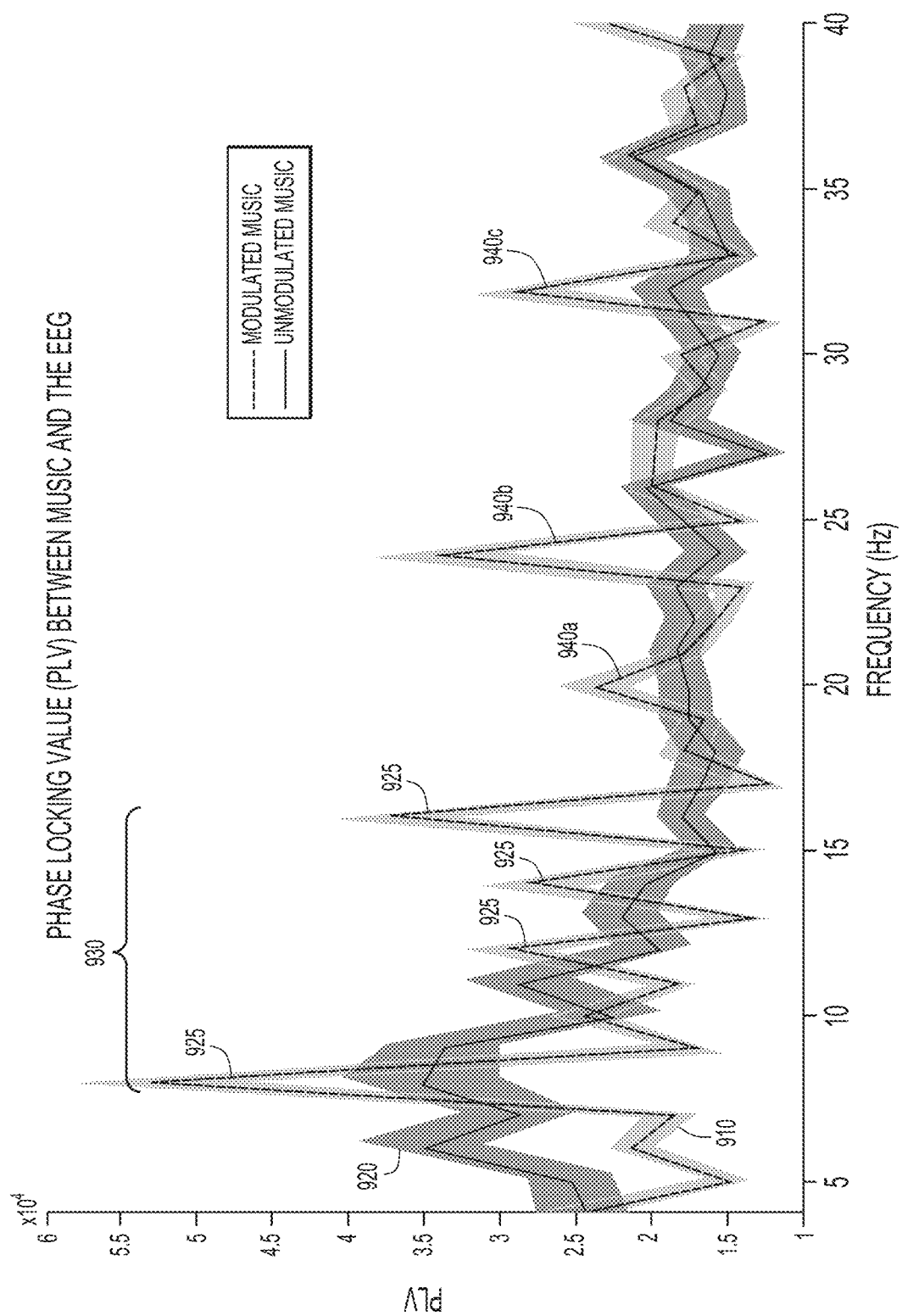
FIG. 9 is a graph comparing the Phase-Locking Value between a modulated acoustic element and the output of an Electroencephalogram to the Phase-Locking Value between an unmodulated acoustic element and the output of an Electroencephalogram, according to example embodiments.

With reference now made to FIG. 9, depicted therein are overtones of neural stimulation modulated signal. Specifically, the phase synchronization between an acoustic signal and the output of an Electroencephalogram (EEG) is illustrated. Phase-Locking Value (PLV) is a statistic that looks at the relationship between two signals, while an EEG measures brain activity. Accordingly, the PLV may be used to investigate task-induced changes in long range synchronization of neural activity. Specifically, the PLV statistic may be used as a proxy for connectivity. If the two signals rise and fall together more than a baseline value, then there is more synchronization or loosely speaking, enhanced connectivity between these two signals. Accordingly, spikes in the PLV 910 between EEG values and acoustic signals may be considered an indication of entrainment of the neural signals by the acoustic signal at the frequency where the spike arises. The analysis of FIG. 9 graphs the PLV of an acoustic signal with an EEG signal. The solid line 910 graphs the PLV for a modulated acoustic signal versus the EEG of the listener, while the dashed line 920 graphs the PLV for an unmodulated acoustic signal versus the EEG of the listener. There are peaks 925 at the modulation rates used in the stimulation session 930: 8 Hz, 12 Hz, 14 Hz and 16 Hz. Overtones, such as overtones 940a-c, start to show up immediately after region 930 and may continue throughout to much higher frequency ranges.

Brain imaging data has shown that neural stimulation based upon complex waveforms results in broader stimulation of neural oscillatory overtones far past the range of stimulation due to the presence of overtones, such as the spikes 940a-c of FIG. 9. Accordingly, waveform protocol 259 of FIG. 2 may be configured to provide waveforms to stimulation protocol 260 that are configured to provide stimulation past the range of stimulation via overtones.

Waveform protocol 259 of FIG. 2 may also be configured to provide waveforms that target specific areas of the brain. Since the waveform is enhanced using the present invention, there is a unique opportunity to target actual regions of the brain. Neural oscillatory waveforms differ dramatically depending on the region of the brain being measured. Different regions of the brain exhibit different waveform shapes in their neural oscillations. Even if two brain regions are firing at the exact same rate, the purpose of the oscillation may be very different, and the different purpose may be expressed through different waveforms. Matching the waveform of the stimulation to the brain region being targeted may enhance the effectiveness of neural stimulation and may enhance the targeting of specific brain regions.

With reference now made to FIGS. 10A and 10B, depicted therein are example embodiments of waveforms generated by waveform protocol 259 of FIG. 2 configured to target and enhance neural stimulation for specific areas of the brain. Illustrated in FIG. 10A are the EEG output measured from different regions on the brain. Alpha neural oscillations (which range from 8-12 Hz) are prevalent all through the brain, but serve different purposes in different areas. Even if two brain regions are firing at the exact same rate, the purpose of the oscillation could be very different. This difference in purpose of effect is often expressed through specific waveforms. 10 Hz oscillations measured from the frontal cortex 1010 look very different from the same oscillations rate taken from the motor cortex 1020. The motor cortex oscillations 1020 have an "M"-like shape to them among other features quite different from the frontal cortex oscillations 1010 which are relatively smoother. By using modulation waveforms that generally mimic the shape of specific areas of the brain, neural stimulation of such specific areas of the brain may be enhanced. FIG. 10B illustrates examples of such modulation waveforms configured to target the frontal cortex 1030 and the motor cortex 1040.

Specifically, waveform 1030 is configured to enhance neural stimulation of the frontal cortex, and therefore, is shaped to mimic the shape of frontal cortex oscillations 1010. Accordingly, waveform 1030 is provided with a relatively smooth shape, in this case, a shape similar to that of a sine wave. Waveform 1040 is configured to enhance neural stimulation of the motor cortex, and therefore, is shaped to mimic the "M"-like shape of motor cortex oscillations 1020.

If a user decides to generate a stimulation protocol to help ease anxiety by stimulating 10 Hz in the frontal regions of the brain, a stimulation protocol may be generated to use the frontal waveform 1030 at a rate of 10 Hz. The modulation could be applied to one or more audio files, and played for the user. This process would be much more effective than using a single modulation waveform for all purposes.

Figure 11:
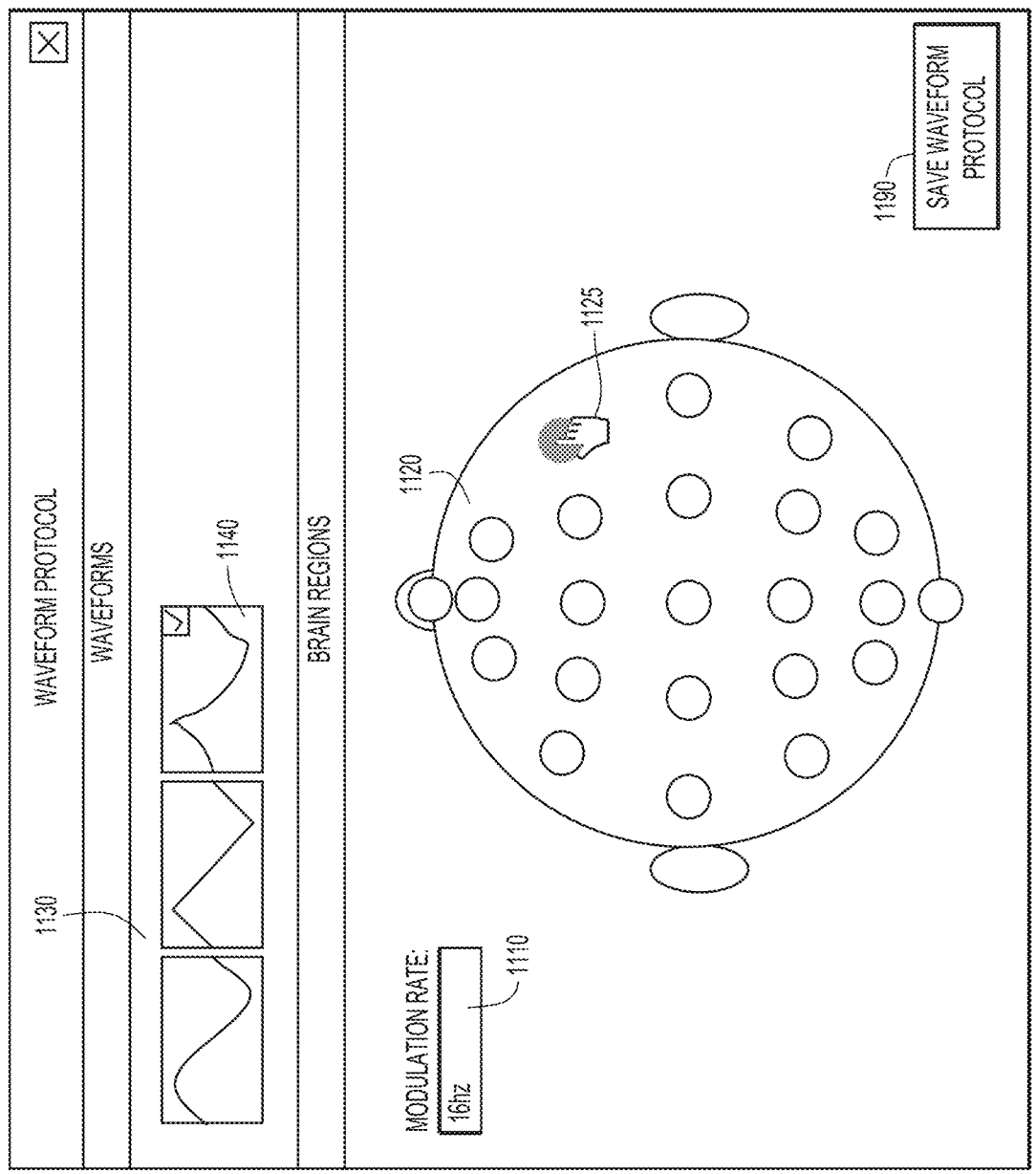
FIG. 11 is an illustration of a software user interface used to generate stimulation waveforms that target specific areas of a brain for noninvasive neural stimulation using audio, according to example embodiments.

Waveform protocol 259 of FIG. 2 may be implemented through a software interface like that illustrated in FIG. 11. FIG. 11 depicts an example software interface 1100 that may be used to generate or create a waveform protocol, which controls the waveform or waveforms used in the stimulation protocol 260 of FIG. 2. In the example of FIG. 11, a waveform is associated with a modulation rate. This means that when a certain modulation rate is being used it will automatically be used in conjunction with the associated modulation waveform. A user may enter the desired modulation rate to be associated with the waveform protocol in the Modulation Rate textbox field 1110. Next, a depiction of the head and a typical EEG sensor array 1120 is presented to the user. Array 1120 allows the user to select a sensor 1125 and retrieve a list of typical neural oscillatory waveforms for that modulation rate (entered in text box 1110) and brain region 1130. If the user selects the frontal cortex, included in list 1130 would be the relative smooth waveform 1030 of FIG. 10. Similarly, if the user selects the motor cortex, included in list 1130 would be the "M"-like shaped waveform 1040 of FIG. 10. The user may then select the desired waveform 1140, and save the protocol via selection button 1190. This waveform protocol may then be provided to stimulation protocol 260 of FIG. 2.

Returning to FIG. 2, once stimulation protocol 260 has been generated, a protocol that may take into account the output of one or more of beat detector 202 and waveform protocol 259, the protocol is provided to modulator 250.

The stimulation protocol 260 specifies the duration of the auditory stimulation, as well as the desired stimulation across that timeframe. To control the stimulation, it continually instructs the modulator 250 as to the rate, depth, waveform and phase of the modulations. As described above, the stimulation protocol 260 may instruct modulator 250 based upon the output of beat detector 220 to ensure the rates are multiples or factors of the BPM measured by rhythmic content in the audio elements 202. As also described above, a modulation waveform may be specified in the waveform protocol 259, and is used to effect neural oscillatory overtones and/or to target specific brain regions, which is provided to modulator 250 via stimulation protocol 260. Finally, modulation phase control of modulator 250 may be provided by stimulation protocol 260 based upon beat detector 220 to ensure the phase of modulation matches the phase of rhythmic content in the audio elements 202. Modulation depth control is used to manipulate the intensity of the stimulation.

The modulator 250 may use a low-frequency oscillator according to the stimulation protocol 260, which contains ongoing rate, phase, depth, and waveform instruction. Low frequency oscillation (LFO) is a technique where an additional oscillator, that operates at a lower frequency that the signal being modulated, modulates the audio signal, thus causing a difference to be heard in the signal without the actual introduction of another sound source. LFO is commonly used by electronic musicians to add vibrato or various effects to a melody. In this case it is used to modulate the amplitude, frequency, stereo panning or filters according to the stimulation protocol 260.

The modulator 250 is used to modulate frequency components 240 and unfiltered audio elements 243. Frequency components 240 are modulated and then mixed with their counterpart unmodulated components 242 in mixer 251 to produce final filtered, modulated audio elements 252, which are then sent to the audio arranger 253. Audio elements 243, on the other hand, are modulated in full, so they need not be remixed, and are therefore sent directly to the audio arranger 253.

An "audio arranger" is a device or process that allows a user to define a number of audio components to fill an audio composition with music wherever the score has no implicit notes. Accordingly, audio arranger 253 arranges all audio content across the timeline of the stimulation protocol 260. As illustrated in FIG. 2, stimulation protocol 260 sends its timeframe to the audio arranger 253. In essence, audio arranger 253 creates the final audio arrangement. Most importantly, audio arranger 253 ensures that modulated content is always present, and is always coupled with unmodulated content. Filtered, modulated audio elements 252 automatically contain modulated and unmodulated content, but audio arranger 253 must still arrange them for maximum coverage across the timeline. Modulated audio elements 254 and unmodulated audio elements 244 must be arranged such that a modulated element is always paired with an unmodulated element, and that there are always at least two elements present throughout the timeline.

Figure 12:
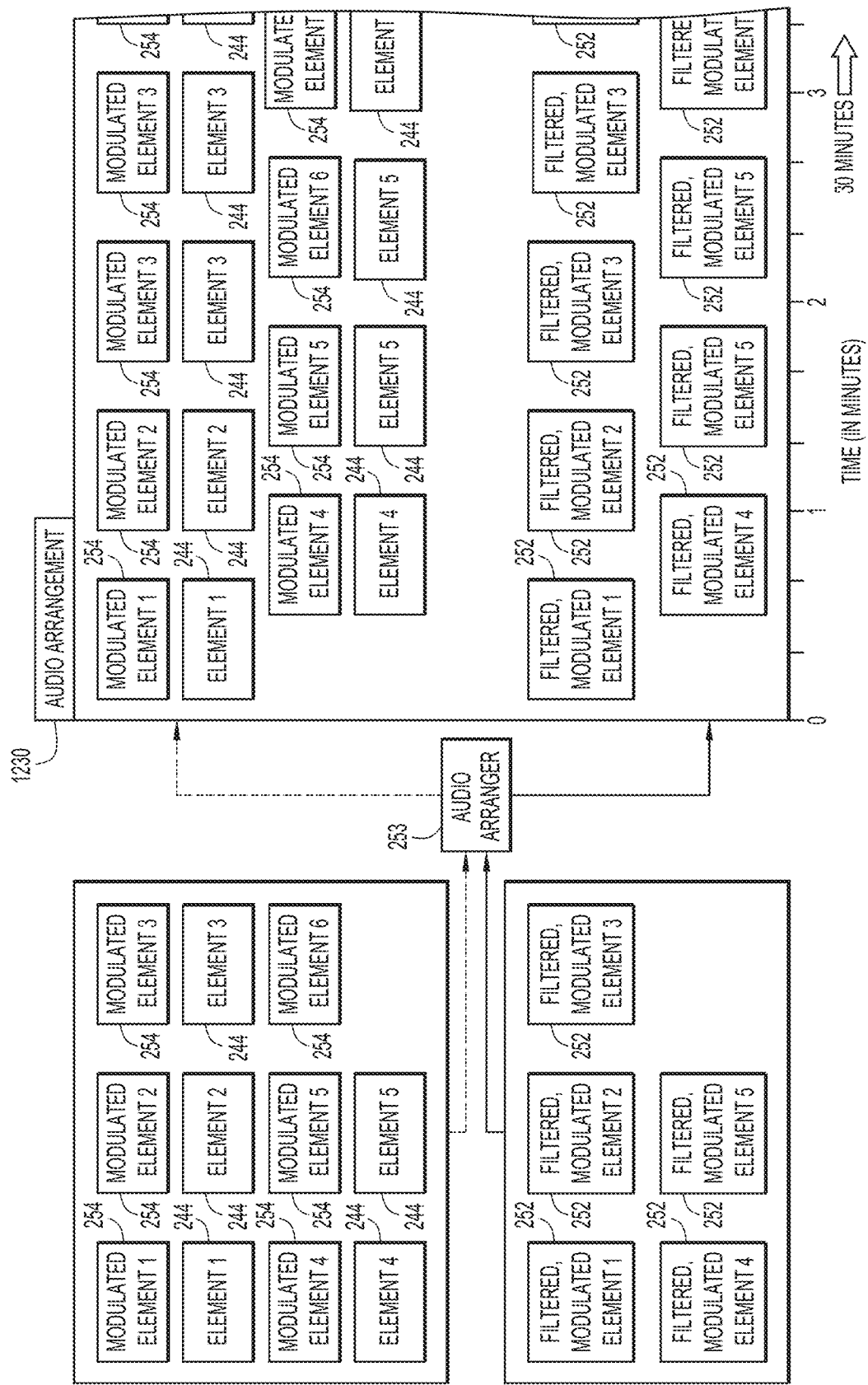
FIG. 12 is functional diagram of an audio arranger used in noninvasive neural stimulation using audio, according to example embodiments.

Illustrated in FIG. 12 is a logical flow chart of the computer functions to be performed by audio arranger 253. As noted above, the job of the audio arranger 253 is to ensure that modulated audio is always paired with unmodulated audio, as well as ensuring an even distribution of available audio content. Audio elements, both modulated 254 and unmodulated 244, will be sent to the audio arranger 253, along with filtered and modulated elements 252. Audio arranger 253 then distributes the audio elements evenly across the span of the arrangement 1230. Audio arranger 253 also ensures that modulated elements 254 are always paired with unmodulated audio 254. For filtered, modulated audio elements 252, audio arranger 253 doesn't need to worry about pairing modulated and unmodulated content, since the filter already separated frequency components such that each element already contains modulated and unmodulated components, so audio arranger 253 need only distribute the elements evenly 252. For example, audio arranger 253 may distribute the elements such that such that at least 50% of the stimulation timeline of the arranged audio file contains modulated frequency components.

Returning to FIG. 12, once arrangement is complete, the arranged audio element is sent to the final mixdown 270 which provides a final mixdown and encodes the full audio onto an electronic medium. "Final mixdown" refers to the final output of a multi-track audio arrangement A multitrack recording is anything with more than one individual track, or more than one piece of audio layered on top of another, to be played simultaneously. The final output of multitrack audio is also known as the mixdown.

Figure 13:
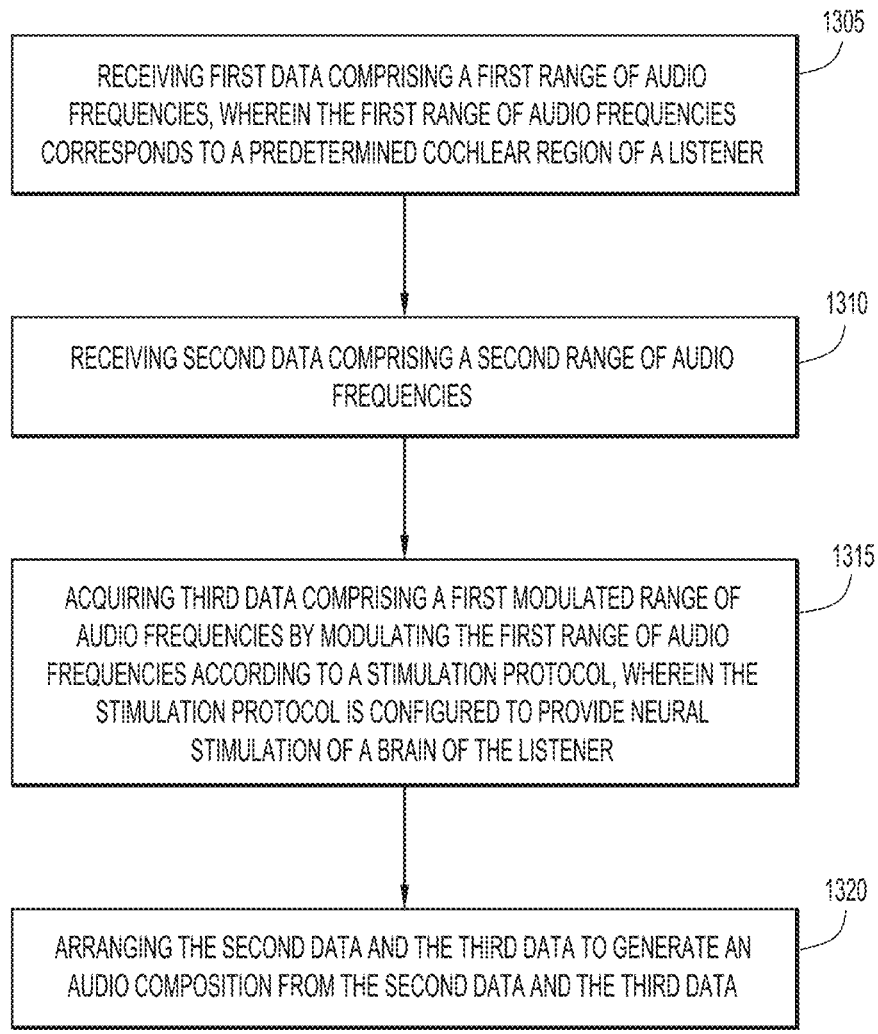
FIG. 13 is a flowchart illustrating a process flow for providing the noninvasive neural stimulation using audio techniques, according to example embodiments.

With reference now made to FIG. 13, depicted therein is a flowchart 1300 illustrating an exemplary process flow according to the techniques described herein. The process begins in operation 1305 where first data comprising a first range of audio frequencies is received. The first range of frequencies corresponds to a predetermined cochlear region of the listener. In operation 1310, second data, comprising a second range of frequencies, is received. Examples of operations 1305 and 1310 may include any combinations of operations corresponding to one or more of operations of 240, 242, 243 and 244 of FIG. 2. For example, the first data of operation 1305 may comprise frequency components to modulate 240 of FIG. 2 that have been filtered out of an audio element by filter 230. According to other example embodiments, the first data of operation 1305 may comprise audio elements to modulate 243 that have been separated audio separator 232 of FIG. 2. According to still other example embodiments, the first data in operation 1305 may comprises a combination of frequency components to modulate 240 and audio elements to modulate 243 of FIG. 2. Example embodiments of the second data of operation 1310 may comprises frequency components not to modulate 242 of FIG. 2, audio elements not to modulate 244 also of FIG. 2, or a combination thereof.

In operation 1310, third data is acquired that corresponds to a first modulated range of audio frequencies. The third data is acquired by modulating the first range of audio frequencies according to a stimulation protocol configured to provide neural stimulation of a brain of a listener. For example, operation 1315 may include the modulation by modulator 250 of frequency components to modulate 240 and/or audio elements to modulate 243 according to stimulation protocol 260, as illustrated in FIG. 2.

In operation 1320, the second data and third data are arranged to generate an audio composition from the second data and the third data. For example, operation 1320 may include the operations carried out by mixer 251 and/or audio arranger 253 of FIG. 2.

FIG. 14 illustrates a hardware block diagram of a computing device 1400 that may perform the functions of any of the computing or control entities referred to herein in connection with noninvasive neural stimulation through audio. It should be appreciated that FIG. 14 provides only an illustration of one embodiment and does not imply any limitations with regard to the environments in which different embodiments may be implemented. Many modifications to the depicted environment may be made.

As depicted, the device 1400 includes a bus 1412, which provides communications between computer processor(s) 1414, memory 1416, persistent storage 1418, communications unit 1420, and input/output (I/O) interface(s) 1422. Bus 1412 can be implemented with any architecture designed for passing data and/or control information between processors (such as microprocessors, communications and network processors, etc.), system memory, peripheral devices, and any other hardware components within a system. For example, bus 1412 can be implemented with one or more buses.

Memory 1416 and persistent storage 1418 are computer readable storage media. In the depicted embodiment, memory 1416 includes random access memory (RAM) 1424 and cache memory 1426. In general, memory 1416 can include any suitable volatile or non-volatile computer readable storage media. Instructions for the "Neural Stimulation Control Logic" may be stored in memory 1416 or memory 1418 for execution by processor(s) 1414. The Neural Stimulation Control Logic stored in memory 1416 or memory 1418 may implement the noninvasive neural stimulation through audio techniques of the present application.

One or more programs may be stored in persistent storage 1418 for execution by one or more of the respective computer processors 1414 via one or more memories of memory 1416. The persistent storage 1418 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 1418 may also be removable. For example, a removable hard drive may be used for persistent storage 1418. Other examples include optical and magnetic disks, thumb drives, and smart cards that are inserted into a drive for transfer onto another computer readable storage medium that is also part of persistent storage 1418.

Communications unit 1420, in these examples, provides for communications with other data processing systems or devices. In these examples, communications unit 1420 includes one or more network interface cards. Communications unit 1420 may provide communications through the use of either or both physical and wireless communications links.

The above description is intended by way of example only. Although the techniques are illustrated and described herein as embodied in one or more specific examples, it is nevertheless not intended to be limited to the details shown, since various modifications and structural changes may be made within the scope and range of equivalents of the claims.

What is claimed is:

1. A method comprising:
    receiving, by a computer processor, first data comprising a first range of audio frequencies, wherein the first range of audio frequencies corresponds to an insensitive cochlear region of a listener;
    receiving, by the computer processor, second data comprising a second range of audio frequencies;
    acquiring, by the computer processor, third data comprising a first modulated range of audio frequencies by modulating the first range of audio frequencies according to a stimulation protocol, wherein the stimulation protocol is configured to provide neural stimulation of a brain of the listener, and wherein acquiring the third data comprises synchronizing the modulating of the first range of audio frequencies with rhythmic acoustic events in the first range of audio frequencies; and
    arranging, by the computer processor, the second data and the third data to generate an audio composition from the second data and the third data.

2. The method of claim 1, wherein receiving the first data and the second data comprises filtering, by the computer processor, an audio element into the first data comprising the first range of audio frequencies and the second data comprising the second range of audio frequencies; and
    wherein arranging the second data and the third data to generate the audio composition comprises mixing, by the computer processor, the first modulated range of audio frequencies and the second range of audio frequencies.

3. The method of claim 1, where receiving the first data comprises receiving, by the computer processor, a first audio element and receiving the second data comprises receiving, by the computer processor, a second audio element.

4. The method of claim 1, wherein the first data comprises data from one or more of a digital audio file, an analog audio file, or a live recording.

5. The method of claim 1, wherein the first range of audio frequencies comprises a range of audio frequencies between 0 Hz and 1500 Hz, inclusive, a range of audio frequencies between 8 kHz and 20 kHz, inclusive, or a range of audio frequencies between 5 kHz and 6.5 kHz, inclusive.

6. The method of claim 1, wherein the first range of audio frequencies comprises a high range of audio frequencies and a low range of audio frequencies, and wherein the high range of audio frequencies and the low range of audio frequencies are not continuous and are not overlapping.

7. The method of claim 6, wherein acquiring the third data comprising the first modulated range of audio frequencies comprises modulating, by the computer processor, the high range of audio frequencies and the low range of audio frequencies in the same way using one or more of a same waveform, a same phase and/or a same rate.

8. The method of claim 1, wherein acquiring the third data comprising the first modulated range of audio frequencies comprises applying, by the computer processor, a modulation waveform selected according to a region of the brain of the listener to which the neural stimulation is to be targeted.

9. The method of claim 1, wherein modulating the first range of audio frequencies comprises altering, by the computer processor, the depth of modulation with time.

10. The method of claim 1, wherein modulating the first range of audio frequencies comprises applying, by the computer processor, amplitude modulation to the first range of audio frequencies.

11. An apparatus comprising:
a memory, and
a processor, wherein the processor is configured to:
receive and store in the memory first data comprising a first range of audio frequencies, wherein the first range of audio frequencies corresponds to an insensitive cochlear region of a listener;
receive and store in the memory second data comprising a second range of audio frequencies;
acquire third data comprising a first modulated range of audio frequencies by modulating the first range of audio frequencies according to a stimulation protocol, wherein the stimulation protocol is configured to provide neural stimulation of a brain of the listener, and wherein the third data is acquired by synchronizing the modulating of the first range of audio frequencies with rhythmic acoustic events in the first range of audio frequencies; and
arrange the second data and the third data to generate an audio composition from the second data and the third data.

12. The apparatus of claim 11, wherein the processor is configured to receive the first data and the second data by filtering an audio element into the first data and the second data; and
wherein the processor is configured to arrange the second data and the third data to generate the audio composition by mixing the first modulated range of audio frequencies and the second range of audio frequencies.

13. The apparatus of claim 11, wherein the processor is configured to receive the first data by receiving a first audio element; and
wherein the processor is configured to receive the second data by receiving a second audio element.

14. The apparatus of claim 11, wherein the processor is configured to acquire the third data by applying a modulation waveform selected according to a region of the brain of the listener to which the neural stimulation is to be targeted.

15. A tangible, non-transitory computer readable media encoded with instructions, wherein the instruction, when executed by a processor, are configured to:
receive first data comprising a first range of audio frequencies, wherein the first range of audio frequencies corresponds to an insensitive cochlear region of a listener;
receive second data comprising a second range of audio frequencies;
acquire third data comprising a first modulated range of audio frequencies by modulating the first range of audio frequencies according to a stimulation protocol, wherein the stimulation protocol is configured to provide neural stimulation of a brain of the listener, and wherein the third data is acquired by applying a modulation waveform selected according to a region of the brain of the listener to which the neural stimulation is to be targeted; and
arrange the second data and the third data to generate an audio composition from the second data and the third data.

16. The tangible, non-transitory computer readable media of claim 15, wherein the instructions are further operable to receive the first data and the second data by filtering an audio element into the first data and the second data; and
wherein the instructions are further operable to arrange the second data and the third data to generate the audio composition by mixing the first modulated range of audio frequencies and the second range of audio frequencies.

17. The tangible, non-transitory computer readable media of claim 15, wherein the instructions are further operable to receive the first data by receiving a first audio element; and
wherein the instructions are further operable to receive the second data by receiving a second audio element.

18. An apparatus comprising:
a memory, and
a processor, wherein the processor is configured to:
receive and store in the memory first data comprising a first range of audio frequencies, wherein the first range of audio frequencies corresponds to an insensitive cochlear region of a listener;
receive and store in the memory second data comprising a second range of audio frequencies;
acquire third data comprising a first modulated range of audio frequencies by modulating the first range of audio frequencies according to a stimulation protocol, wherein the stimulation protocol is configured to provide neural stimulation of a brain of the listener, and wherein the third data is acquired by applying a modulation waveform selected according to a region of the brain of the listener to which the neural stimulation is to be targeted; and
arrange the second data and the third data to generate an audio composition from the second data and the third data.

* * * * *